United States Patent [19]

Magee, Jr. et al.

[11] Patent Number: 5,118,403
[45] Date of Patent: Jun. 2, 1992

[54] GLASSY CARBON LINEAR ARRAY ELECTRODE

[75] Inventors: Leo J. Magee, Jr., Guilderland; Janet G. Osteryoung, Snyder, both of N.Y.

[73] Assignee: The Research Foundation of State Univ. of N.Y., Albany, N.Y.

[21] Appl. No.: 364,204

[22] Filed: Jun. 9, 1989

[51] Int. Cl.$^5$ .............................................. G01N 27/30
[52] U.S. Cl. ................................... 204/400; 73/61.1 C; 73/61.52; 204/294; 204/409; 204/411; 204/412; 210/656
[58] Field of Search ........ 204/294, 400, 412, 416–419, 204/409, 411

[56] References Cited

U.S. PATENT DOCUMENTS

| | | | |
|---|---|---|---|
| 3,202,596 | 8/1965 | Canevari | 204/197 |
| 3,337,440 | 8/1967 | Nestor | 204/404 |
| 4,233,031 | 11/1980 | Matson et al. | 204/412 |

OTHER PUBLICATIONS

Wang et al., "Ensembler of Carbon Paste Ultramicroelectrodes", *J. Electroanal. Chem.*, 249 (1988), pp. 339–345.
D. E. Weisshaar et al., *Kel-F-Graphite Composite Electrode as an Electrochemical Detector for Liquid Chromatography and Application to Phenolic Compounds*, 53 Anal. Chem. 1809 (1981).
L. Falat et al., *Voltammetric Differentiation of Ascorbic Acid and Dopamine at an Electrochemically Treated Graphite/Epoxy Electrode*, 54 Anal. Chem. 2108 (1982).
J. Wang et al., *Vitreous Carbon-Based Composite Electrode as an Electrochemical Detector for Liquid Chromatography*, 298 J. Chromatogr. 79 (1984).
W. L. Caudill et al., *Flow Rate Independent Amperometric Cell*, 54 Anal. Chem. 2532 (1982).
A. M. Bond et al., *Theory and Experimental Characterization of Linear Gold Microelectrodes with Submicrometer Thickness*, 90 J. Phys. Chem. 2911 (1986).
W. Thormann et al., *Voltammetry at Linear Gold and Platinum Microelectrode Arrays Produced by Lithographic Techniques*, 57 Anal. Chem. 2764 (1985).
L. E. Fosdick et al., *Optimization of Microelectrode Array Geometry in a Rectangular Flow Channel Detector*, 58 Anal. Chem. 2481 (1986).
L. E. Fosdick et al., *Amperometric Response of Microlithographically Fabricated Microelectrode Array Flow Sensors in a Thin-Layer Channel*, 58 Anal. Chem. 2750 (1986).
M. DeAbreu et al., =-Gold-Electrode-Array Thin-Layer Flow Cell, 59 Anal. Chem. 204 (1987).
S. Moldoveanu et al., *Numerical Simulation of Convective Diffusion at a Microarray Channel Electrode*, 185 J. Electroanal. Chem. 239 (1985).
J. L. Anderson et al., *Hydrodynamic Voltammetry at an Interdigitated Electrode Array in a Flow Channel, Part 1. Numerical Simulation*, 196 J. Electroanal. Chem. 213 (1985).
D. K. Cope et al., *Calculation of Convective-Diffusion Current at Multiple Strip Electrodes in a Rectangular Flow Channel, Implications for Electrochemical Detection*, 205 J. Electroanal. Chem. 101 (1986).
E. M. Sparrow, *Analysis of Laminar Forced Convection Heat Transfer in Entrance Region of Flat Rectangular Ducts*, National Advisory Committee for Aeronautics TN 3331, (1955).
S. G. Weber et al., *The Behavior of an Electrochemical Detector Used in Liquid Chromatography and Continuous Flow Voltammetry, Part 1. Mass Transport-limited Current*, 100 Anal. Chim. Acta 531 (1978).
R. A. J. Sambell et al., *Carbon Fiber Composites with Ceramic and Glass Matrixes. 1. Discontinuous Fibers*, 7 J. Mater. Sci. 663 (1972).
R. A. J. Sambell et al., *Carbon Fiber Composites with Ceramic and Glass Matrixes. 2. Continuous Fibers*, 7 J. Mater. Sci. 676 (1972).

*Primary Examiner*—T. Tung

[57] ABSTRACT

A linear array electrode is provided for use in a flowcell detector. The electrode includes an electrically conductive material grooved to form array elements. The conductive material is embedded in an electrically insulating embedment such that a surface of each array element is exposed. The electrode includes means for connecting the electrically conductive material to a source of electric potential.

13 Claims, 5 Drawing Sheets

GLASSY CARBON LINEAR ARRAY ELECTRODE

Work leading to this invention was supported in part by the National Science Foundation under grant CHE 8521200. The United States Government may have certain rights to this invention.

BACKGROUND OF THE INVENTION

The present invention relates generally to electrochemical detection for liquid chromatography, more particularly to flowcell detectors, and more specifically to a new working electrode for use in a flowcell detector.

Arrays of electrodes for use as electrochemical detectors in flowcells are the subject of many ongoing investigations. Originally developed to take advantage of the properties displayed by microelectrodes (i.e. enhanced current densities from non-planar diffusional contributions to the net current, low iR drop characteristics and a decreased dependence on convection) and to generate larger, more easily measured currents, arrays of electrodes have been fabricated from various materials and in different geometric configurations. See, e.g., Weisshaar, D. E., Tallman, D. E., Anderson, J. L., *Kel-F - Graphite Composite Electrode as an Electrochemical Detector for Liquid Chromatography and Application to Phenolic Compounds,* 53 Anal. Chem. 1809 (1981); Falat, L., Cheng, H. Y., *Voltammetric Differentiation of Ascorbic Acid and Dopamine at an Electrochemically Treated Graphite/Epoxy Electrode,* 54 Anal. Chem. 2109 (1982); Wang, J., Freiha, B. A., *Vitreous Carbon-Based Composite Electrode as an Electrochemical Detector for Liquid Chromatography,* 298 J. Chromatogr. 79 (1984); Caudill, W. L., Howell, J. O., Wightman, R. M., 54 Anal. Chem. 2531 (1982); Bond, A. M., Henderson, T. L. E., Thorman, W., *Theory and Experimental Characterization of Linear Gold Microelectrodes with Submicrometer Thickness.* 90 J. Phys. Chem. 2911 (1986); Thorman, W., van den Bosch, P., Bond, A. M., *Voltammetry at Linear Gold and Platinum Microelectrode Arrays Produced by Lithographic Techniques,* 57 Anal. Chem. 2764 (1985); Fosdick, L. E., Anderson, J. L., *Optimization of Microelectrode Array Geometry in a Rectangular Flow Channel Detector,* 58 Anal. Chem. 2481 (1986); Fosdick, L. E., Anderson, J. L., Baginski, T. A., Jaeger, R. C., *Amperometric Response of Microlithographically Fabricated Microelectrode Array Flow Sensors in a Thin-Layer Channel,* 58 Anal. Chem. 2750 (1986); DeAbreu, M., Purdy, W. C., *32-Gold-Electrode-Array Thin-Layer Flow Cell,* 59 Anal. Chem. 204 (1987). Because of the low dead volumes required of flowcell detectors, under conditions typical of liquid chromatography or flow injection analysis, the linear velocities of the fluids flowing through them are usually too high for non-planar diffusion to be a factor (non-planar diffusion is diffusion toward the electrode from the solution from multiple directions in addition to a normal direction). Only in extreme cases (very low flow rates and extremely small electrode size) will non-planar diffusion affect the measured currents in these flowcell detectors.

Nevertheless, measured current densities of electrode arrays are almost always greater than those obtained for single electrodes of similar active electrode surface area under identical hydrodynamic conditions. This increase in current density is attributed to the re-establishment of the bulk concentration of the electroactive species depleted by electrochemical reaction at an electrode element as the solution containing the species travels across the insulating regions between electrode elements of the array. Moldoveanu, S., Anderson, J. L., *Numerical Simulation of Convective Diffusion at a Microarray Channel Electrode,* 185 J. Electroanal. Chem. 239 (1985); Anderson, J. L., Ou, T. S., Moldoveanu, S., *Hydrodynamic Voltammetry at an Interdigitated Electrode Array in a Flow Channel, Part 1. Numerical Simulation,* 196 J. Electroanal. Chem. 213 (1985); Cope, D. S., Tallman, D. E., *Calculation of Convective-Diffusion Current at Multiple Strip Electrodes in a Rectangular Flow Channel, Implications for Electrochemical Detection,* 205 J. Electroanal. 101 (1986). Consequently, each electrode element of the array "sees" bulk or near bulk concentrations. This situation contrasts greatly with the concentration depletion of electroactive material across the surface of a large electrode by electrochemical reaction. Maintenance of bulk density enhances diffusion to the electrode and thus enhances current density. Enhanced current density is desirable because it usually also provides enhanced signal to noise ratios.

Electrode arrays have been fabricated in a number of geometries. The simplest geometry from the standpoint of fabrication is random. Random arrays can be made by combining powders or chips of electrode material with an insulator (e.g., plastic). Weisshaar, D. E., Tallman, D. E., Anderson, J. L., 53 Anal. Chem. 1809 (1981); Falat, L., Cheng, H. Y., 54 Anal. Chem. 2109 (1982). Another type of random array is made using a reticulated electrode material (e.g., reticulated vitreous carbon) with an insulator to fill the pores. Although difficult to characterize geometrically, random arrays are fairly simple to construct from readily available materials. Wang, J., Freiha, B. A., 298 J. Chromatogr. 79 (1984). Arrays of electrodes based on disks have also been fabricated. For example, these arrays have been constructed by sandwiching carbon fibers between glass microscope slides and sealing them in epoxy. Caudill, W. L., Howell, J. O., Wightman, R. M., 54 Anal. Chem. 2531 (1982).

The most popular type of array geometry is the linear array. This electrode geometry is the most efficient in a flowcell when the elements of the electrode array are oriented opposed to the direction of flow, allowing one to obtain the highest current densities and net currents in the space allowed by flowcell dimensions. The most common method for fabricating linear arrays is by thin film technology and lithography. Usually gold is vapor deposited onto a substrate. Bond, A. M., Henderson, T. L. E., Thorman, W., 90 J. Phys. Chem. 2911 (1986); Thorman, W., van den Bosch, P., Bond, A. M., 57 Anal. Chem. 2764 (1985); Fosdick, L. E., Anderson, J. L. 58 Anal. Chem. 2481 (1986); Fosdick, L. E., Anderson, J. L., Baginski, T. A., Jaeger, R. C., 58 Anal. Chem. 2750 (1986). Another method involves etching a pattern in an insulating substrate and filling in the resulting grooves with a gold filler. DeAbreu, M., Purdy, W. C., 59 Anal. Chem. 204 (1987). The major drawbacks of lithographically fabricated arrays based on vapor deposition arise from their three-dimensional nature. The gold lines are on top of the substrate and are on the order of 300–600 nm thick. Apparently no turbulence is caused by these lines in flowcells. However, the layers tend to separate under voltammetric conditions in solution and are mechanically fragile. Thus their utility as something other than laboratory curiosities is limited, because they cannot be subjected to mechanical polishing, a routine procedure for the maintenance of electrodes.

Carbon electrodes, and especially glassy carbon electrodes, are probably the most common type in use today. "Glassy carbon", as used herein, means a relatively hard integral carbon having the ability to be polished to a glassy appearance and having good electrical conductivity. Glassy carbon is particularly described in *Carbon: Electrochemical and Physico-Chemical Properties*, K. Kinoshita, Wiley and Sons (1988). Glassy carbon electrodes are, in fact, the most used electrode type used in flowcells. They are used routinely "as is" or as the substrate for surface-modified and mercury-coated electrodes. Nevertheless, carbon linear arrays are not known to exist in the prior art. Glassy carbon is a very hard, brittle material that shatters quite easily. Though the material is available in a number of shapes and sizes, including rods, plates, disks, tubes, cones and crucibles, the only geometry that has had any extensive use as an electrode material has been the rod. Rods of glassy carbon, typically 3 mm in diameter, are readily sealed in Teflon ®, Kel-F, or some other insulating material to yield a disk electrode of 3 mm diameter. The present invention utilizes machining techniques to produce improved electrode geometries other than a simple disk.

Heretofore a longfelt need has existed for an improved electrode for use in a flowcell detector providing enhanced current density and enhanced signal to noise ratios, and for a method for manufacturing the same.

SUMMARY OF THE INVENTION

The present invention comprises a linear array electrode for use in a flowcell detector, comprising an electrically conductive material grooved to form array elements. The conductive material is embedded in an electrically insulating embedment such that the grooves are filled with insulating material and such that a surface of each array element is exposed. The electrode includes means for connecting the electrically conductive material to a source of electric potential.

Accordingly, an overall object of the invention is to provide a novel and improved working electrode for use in a flowcell detector, e.g., liquid chromatography, flow injection analysis, on-line process monitoring.

A more particular object of the invention is to provide a glassy carbon linear array electrode for use in flowcell detectors which provides enhanced current densities from convective-diffusional regeneration of concentration profiles between elements of the electrode array.

Still another object of the invention is to provide a working electrode for use in a flowcell which enables enhanced current densities from non-planar diffusional contributions to the net current, low iR (current times resistance) drop characteristics and a decreased dependence on convection.

Yet a further object of the invention is to provide a glassy carbon linear array electrode for use as a working electrode in a flowcell detector.

These and other objects of the present invention will be readily apparent from the drawings, written description and appended claims.

DETAILED DESCRIPTION OF THE INVENTION

In accordance with the invention the electrically conductive material may be essentially any such material suitable for electrode use, e.g., platinum, gold, palladium, etc. The insulating material may be essentially any stable high dielectric material which can be made to adhere well to the conductive material. Such materials may include thermoset and thermoplastic resins, e.g., phenolics, epoxies and polyene resins; glasses, glass ceramics and ceramic materials, etc.

The means for connecting the electrically conductive material may be any suitable means such as a wire or metallic strip.

Figure 1:
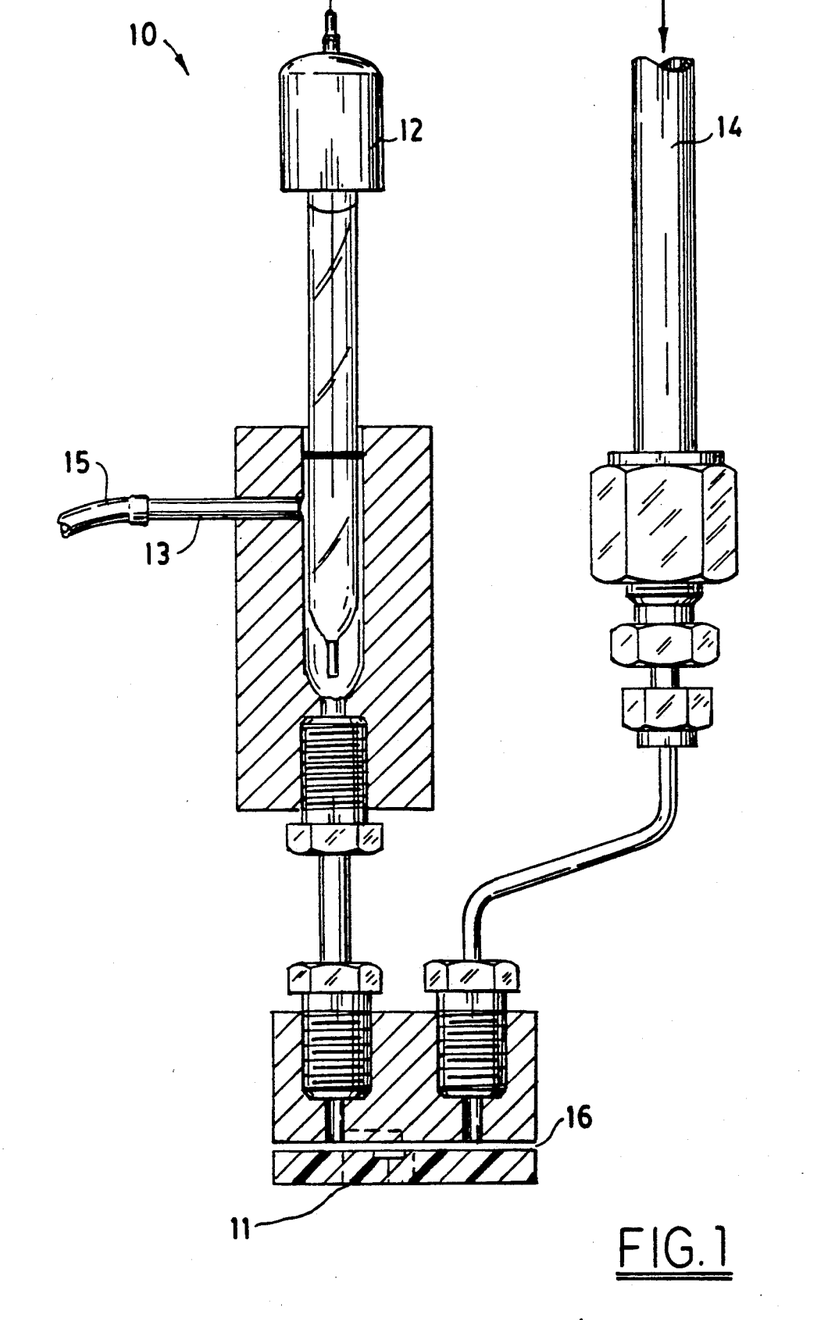
FIG. 1 is a partial sectional view of a standard electrochemical flowcell detector having a working electrode, reference electrode, and auxiliary electrode.
Figure 2:
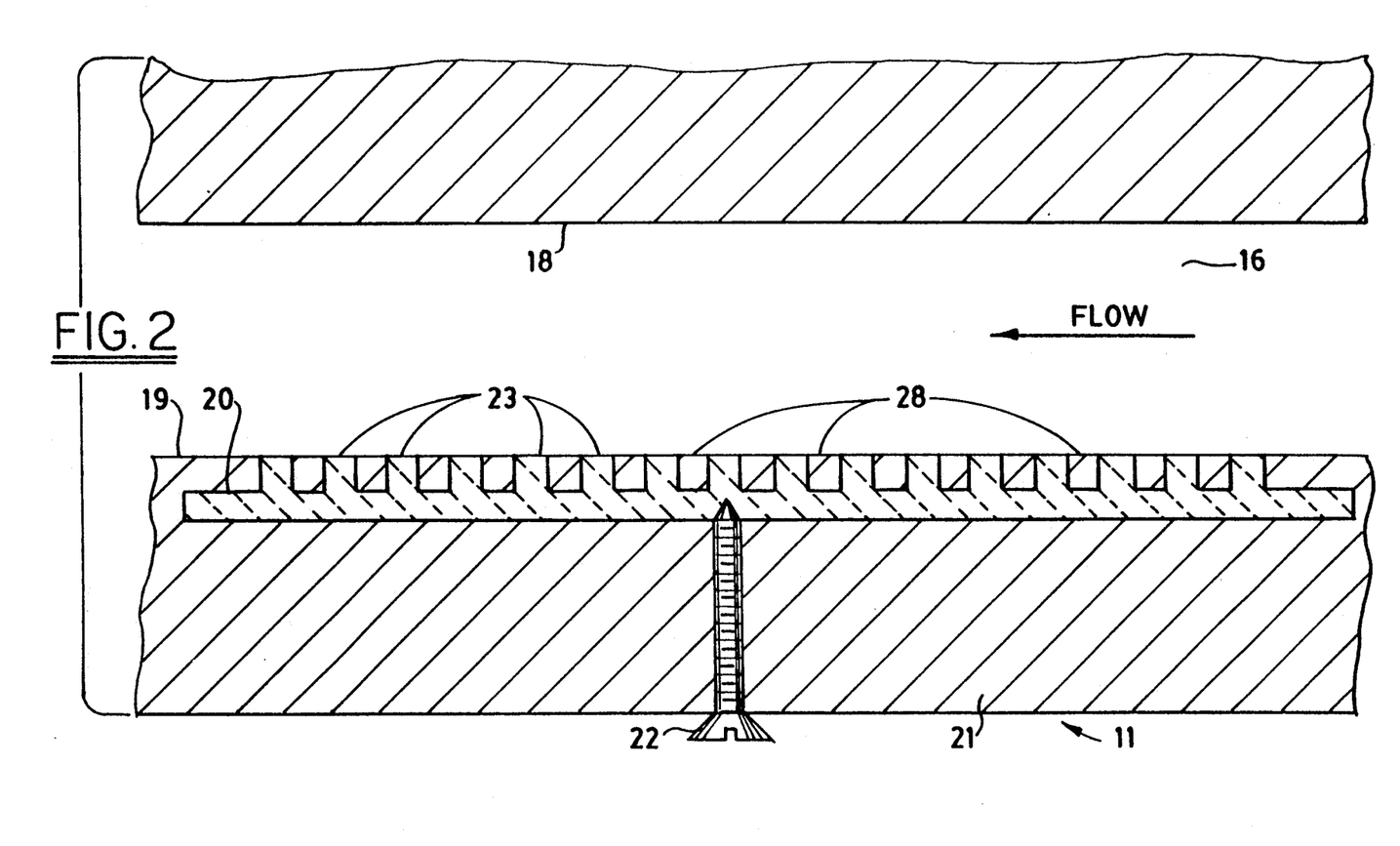
FIG. 2 is an enlarged view of the section of the flowcell shown in FIG. 1.

FIG. 1 illustrates a partial sectional view of a typical electrochemical flowcell detector 10 having working electrode 11, reference electrode 12, and auxiliary electrode 13. A chemical solution to be analyzed enters the flowcell via entrance conduit 14, passes through channel 16, defined by top surface 18 and bottom surface 19 (as shown in FIG. 2). The solution exits the flowcell at exit conduit 15. As is generally known in the art, the potential of electrode array 20 is maintained at a known value with respect to reference electrode 12. The solution to be tested is, of course, in contact with working electrode 11, reference electrode 12, and auxiliary electrode 13. An electroactive substance in the solution will transfer electrons to, or accept electrons from, the external circuit at the surface of the working electrode if the potential is in a characteristic range, dependent upon the identity of the substance. A potentiostat is generally employed to control the potential of the working electrode with respect to the reference electrode by forcing the necessary current through the auxiliary electrode. This current, which also passes through the working electrode, is sampled, differenced, averaged, or subjected to some other manipulation necessary to the analysis. The present invention provides an improved working electrode which enables enhanced current densities in flowcell experiments.

FIG. 2 is an enlarged view of working electrode 11 and flow channel 16. Referring to FIG. 2, working electrode 11 comprises electrode array 20 which is formed of electrically conductive material and includes array elements 23, electrically insulating embedment 21, and means 22 for connecting the electrode array to a source of electrical potential. Electrode array 20 is embedded in electrically insulating embedment 21 such that the top surface of embedment 21 is flush with the top surfaces of array elements 23 and the top surfaces of insulating material 28 in the spaces between elements 23. The chemical solution to be analyzed flows within channel 16 which is bounded by upper surface 18 and lower surface 19 (where lower surface 19 is formed partly by the top surface of embedment 21, the top surfaces of array elements 23 and the top surfaces of the insulating material 28 between array elements 23), and passes over linear array elements 23 of electrode array 20. Array elements 23 of carbon element 20 of the electrode are arranged transversely across channel 16 such that the direction of flow of the solution to be tested is perpendicular to elongated array elements 23.

Figure 3:
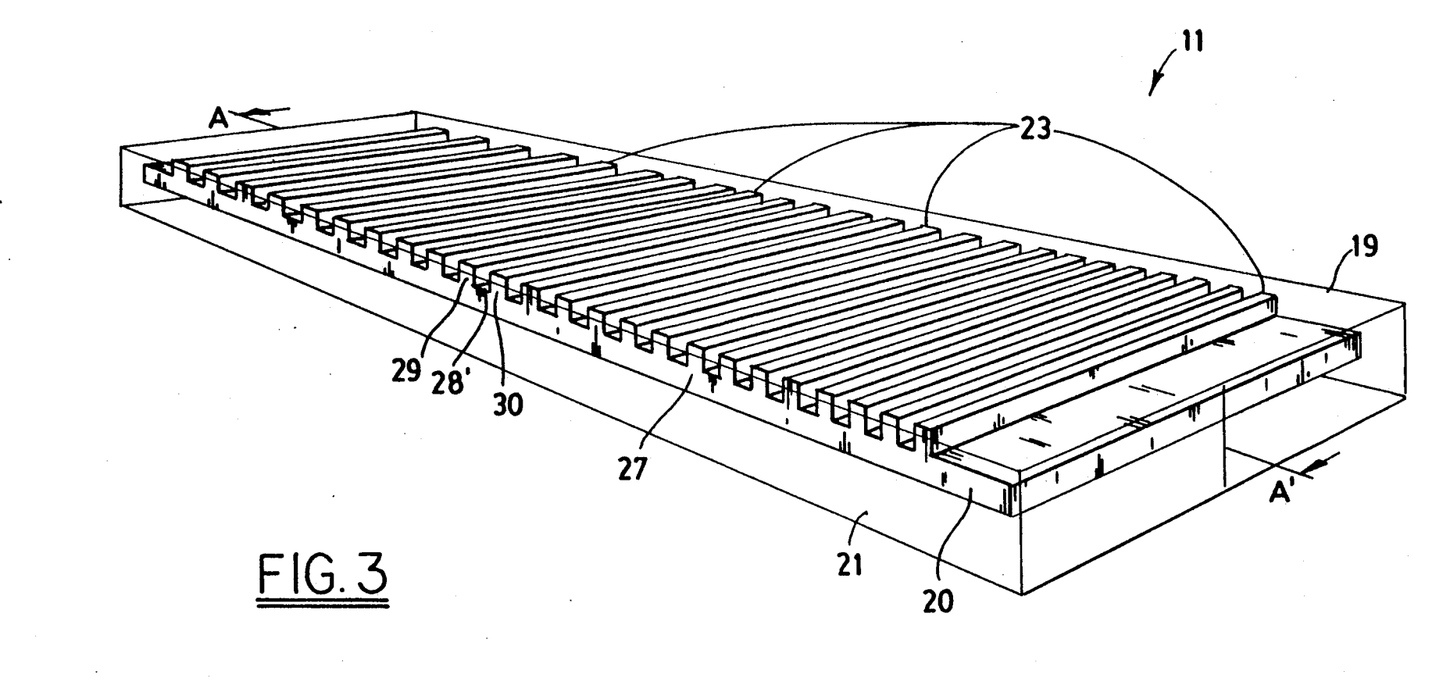
FIG. 3 is a transparent perspective view of the linear array electrode of the invention.
Figure 4:
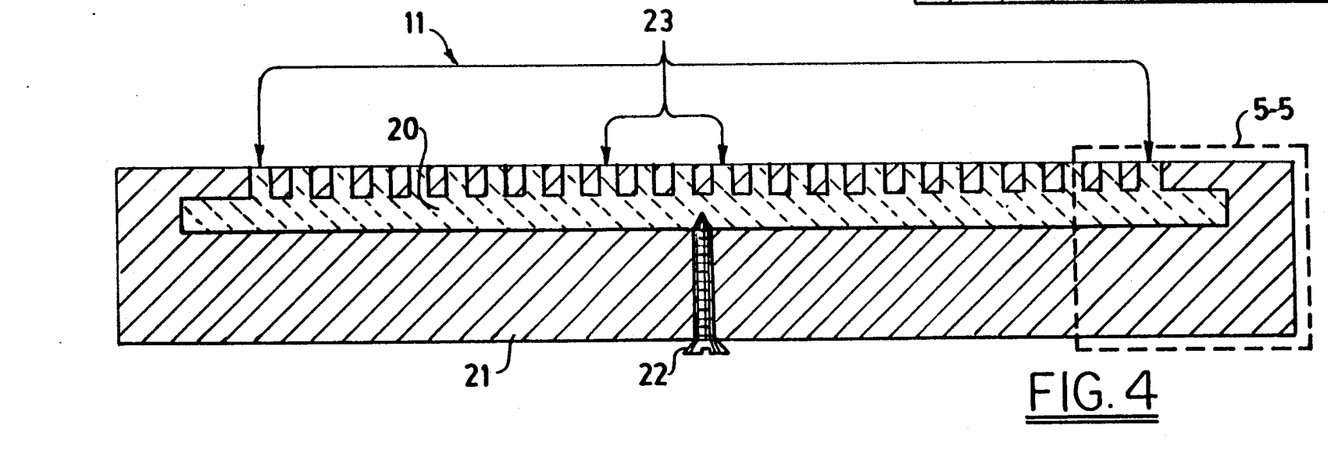
FIG. 4 is a cross-sectional side view of the electrode of FIG. 3 taken along plane 4—4".
Figure 5:
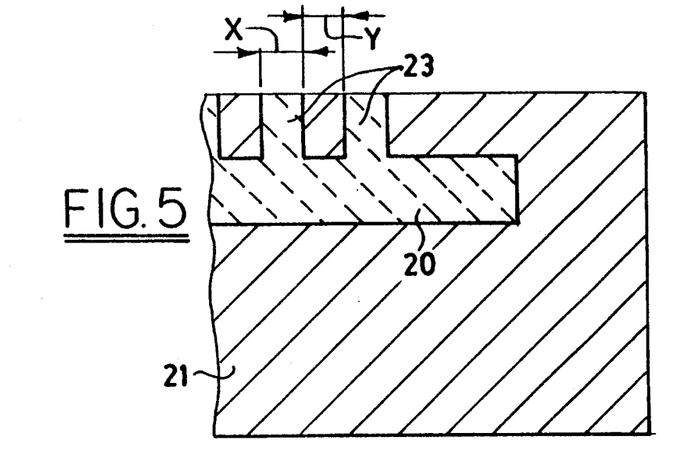
FIG. 5 is an enlarged view of a portion of the electrode of FIG. 4.

FIG. 3 is a transparent perspective view of the glassy carbon linear array electrode of the invention. At the outset it should be clearly understood that the electrode of FIGS. 3-5 is not drawn to scale. Specifically, the grooved portion of electrode array 20 containing array elements 23 has been magnified for illustration purposes. In a preferred embodiment, array 20 comprises generally rectangular base portion 27 and array elements 23 which extend upwardly from base 27. Array elements 23 are separated by a plurality of spaces. For example, array elements 29 and 30 are separated by space 28''. In a preferred embodiment, element 20 is constructed of glassy carbon and embedment 21 is constructed of epoxy, such as Maraglas ® epoxy (available from Acme Chemical and Insulation Co., New Haven, Conn., #658 resin and #558 hardener). Epoxy surrounds and insulates electrode array 20 on all sides such that only the top surfaces of array elements 23 are exposed. Epoxy also fills in all of the spaces 28 between array elements 23. As best shown in FIG. 4, the top surface of array elements 23 are flush with top surface 19 of embedment 21.

FIG. 4 is a cross-sectional side view of the electrode of FIG. 3, taken along plane 4—4''. This figure illustrates the fact that the epoxy of embedment 21 completely surrounds array elements 23 except for the top surfaces of the array elements which are left exposed. Shown in FIG. 4 is means 22 for connecting array 20 to a source of electric potential. Although many suitable electrical connectors will suffice, in a preferred embodiment connecting means 22 comprises a brass screw. An alternative connecting means may comprise a gold contact secured to array 20 and connected to a source of electric potential by a wire conductor.

FIG. 5 is an enlarged view of a portion of the electrode of FIG. 5, illustrating the width "x" of a typical array element and width "y" of a typical space between array elements. The width of an array element is in the range of 10-100 micrometers. As described infra in Table I, one embodiment of the electrode includes array elements having a width ("x") of 60 micrometers and spaces of 65 micrometers ("y"), and a second embodiment includes array elements having a width ("x") of 85 micrometers and spaces of 90 micrometers ("y"). The length of the array elements in both of these embodiments is approximately 4.5 millimeters.

In a preferred embodiment, carbon electrode 11 may be fabricated using glassy carbon plate treated to 2500° C. and available from Atomergic Chemetals, Plainview, New York. Commercially available carbon plates measuring 4''×4'' may be cut into 1''×1'' squares using a dicing saw (such as Tempress model 602, Sola Basic Industries, Los Gatos, California). The cutting is done with a diamond impregnated wheel.

To fabricate the electrode, the glassy carbon plate is placed in the chuck and the depth of cut is set to 0.010 in. A feed rate of approximately 3 in./min. is appropriate. The dicing saw has an automatic feed and jog feature which greatly simplifies the cutting of a plurality of equally spaced grooves into the carbon plate.

After a series of grooves is made in the center of the 1''×1'' plate, the remaining surface is cut back, again using the dicing saw, leaving a series of ridges or array elements in the middle of the plate. The plate is then cut into three equally sized pieces, each of which may be used to make a flowcell detector electrode.

The machined plate is cleaned in an ultrasonic bath to prepare the glassy carbon for sealing in an insulator and to remove any chips and particles remaining in the grooves from machining. The epoxy is poured as a liquid to form the body of the flowcell and to fill the grooves or spaces of the carbon element. Electrical contact is made from the bottom of insulator 21 via brass screw 22. The electrode assembly 11 is prepared for use by first grinding the excess epoxy coating off the glassy carbon with 6700 grit sandpaper. The surface is then polished with alumina/water slurries on a polishing cloth starting with 1μm alumina and working down to 0.05μm alumina for the final polishing.

Experimental Results

Equipment and reagents. The flow system used to characterize the electrodes of the present invention included an LKB model 2150 HPLC pump and a BAS model LC 17A electrochemical flowcell detector with a BAS model LC 4A amperometric detector. The mobile phase was 0.1 M KCl (Malinkrodt reagent grade) in deionized water. The analyte was $K_4Fe(CN)_6 \cdot 3H_2O$ (Baker reagent grade).

Figure 6:
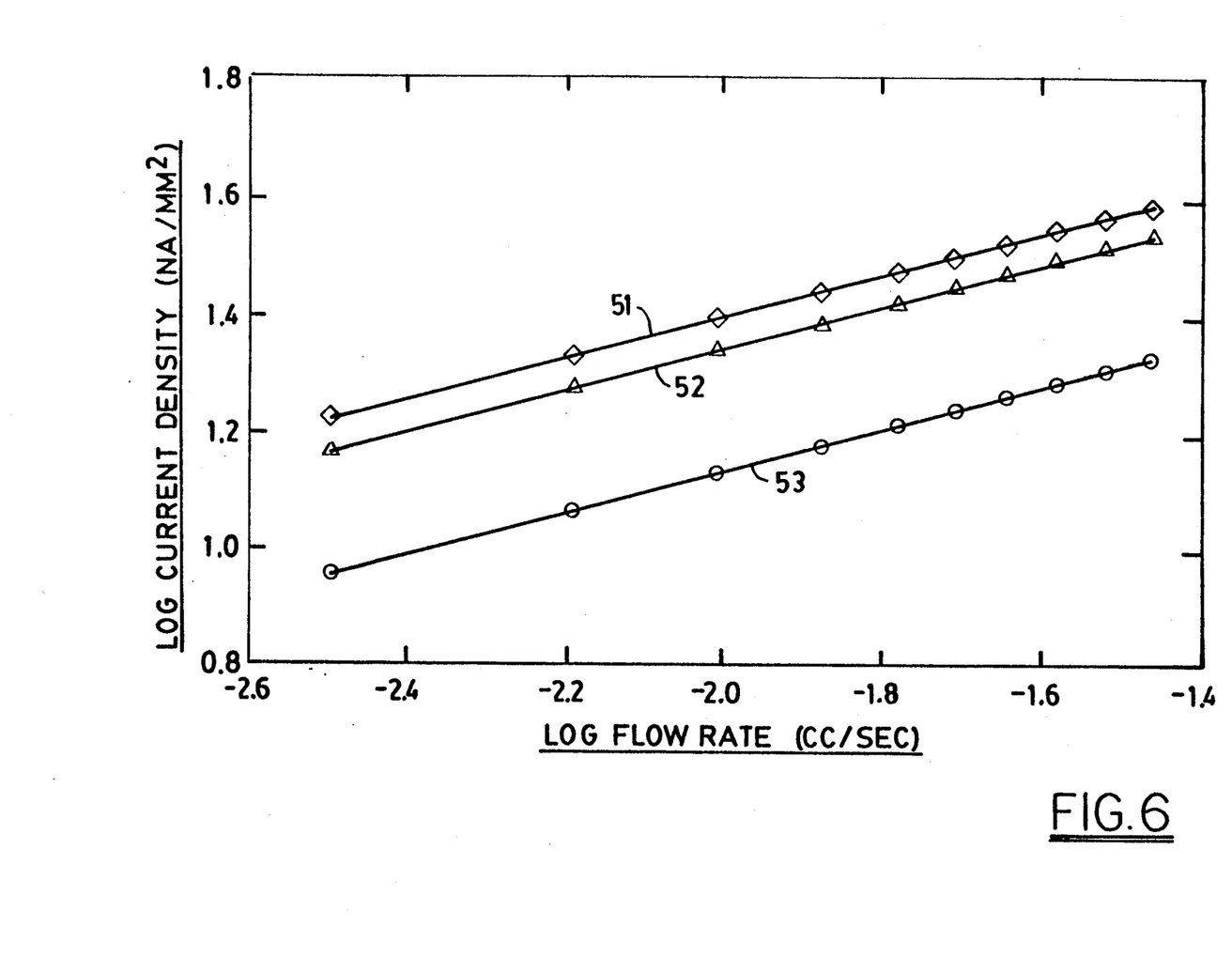
FIG. 6 is a plot of log current vs. log flow rate for two different array electrodes representing the present invention and for one disk electrode of the prior art.

Two different glassy carbon linear array electrodes were fabricated and characterized. The physical characteristics of these two electrodes, as well as the characteristics of the disk electrode with which they are compared, are given in Table I. An experiment was run to determine the current densities of these two electrodes under steady-state conditions, and to compare the results with those obtained for the single disk electrode under similar conditions. This was done by continuously pumping a solution of analyte (4 $\mu$M $Fe(CN)_6^{4-}$) in the mobile phase (0.1 M KCl) through the detector at a series of flow rates. The results of these experiments are given in Table II. As expected, the linear arrays of glassy carbon yielded higher current densities than the single disk. Plots of log current vs. log flow rate using the data of Table II give slopes of 0.36 for the two arrays and 0.34 for the disk electrode. These data are also shown in FIG. 6, where line 51 represents Array I, line 52 represents Array II, and line 53 represents the disk electrode. These slopes agree closely with the one-third power dependence on flow rate established for the channel flowcell (Sparrow, E. M., *Analysis of Laminar Forced Convection Heat Transfer in Entrance Region of Flat Rectangular Ducts*, National Advisory Committee for Aeronautics TN 3331, (1955); Weber, S. G., Purdy, W. C. *The Behavior of an Electrochemical Detector Used in Liquid Chromatography and Continuous Flow Voltammetry, Part 1, Mass Transport-limited Current*, 100 Anal. Chim. Acta 531 (1978).

Photomicrographs taken of the electrodes revealed that the dicing saw is capable of making very small, chip-free array elements in the glassy carbon. Array element widths as small as 60 micrometers in width were obtained at a fairly high feed rate. It should be possible to make even narrower array elements using lower feed rates. Also worthy of note is the versatility of the dicing saw for making cuts of different sizes. Changing the spacing between blade cuts merely requires the setting of a switch on the saw. In addition, gaps of different widths can be made by making multiple cuts with the blade or by using blades of different widths.

The success achieved with the dicing saw in making smooth array elements of glassy carbon in micrometer dimensions in such an easy fashion makes the technique noteworthy. The range of application can probably be extended to other electrode materials such as gold or platinum and to other sealing materials such as other epoxies or Pyrex ® (Sambell, R. A. J., Bowen, D. H., Phillips, D. C., *Carbon Fiber Composites with Ceramic and Glass Matrixes*, 7 J. Mater. Sci. 663 (1972); Sambell, R. A. J., Briggs, A., Phillips, D. C., Bowen, D. H., *Carbon Fiber Composites with Ceramic and Glass Matrixes*, 7 J. Mater. Sci. 676 (1972).

TABLE I

Physical characteristics of two linear array electrodes and a single disk electrode.

|  | ELEMENT WIDTH ($\mu$m) | SPACE WIDTH ($\mu$m) | ELEMENT LENGTH (mm) | NUMBER OF ELEMENTS | TOTAL ACTIVE SURFACE AREA (mm$^2$) |
|---|---|---|---|---|---|
| ARRAY I | 60 | 65 | 4.5 | 24 | 6.48 |
| ARRAY II | 85 | 90 | 4.5 | 21 | 8.03 |
| DISK | | r = 1.5 mm | | 1 | 7.10 |

TABLE II

Steady-state response of a series of electrodes of various geometries (obtained in analysis of 4 $\mu$M solution of $K_4Fe(CN)_6 \cdot 3H_2O$ in 0.05 M KCl.)

| Flow Rate (mL/min) | Current Density (nA/mm$^2$) | | |
|---|---|---|---|
| | Disk | Array I | Array II |
| 0.2 | 9.18 | 16.67 | 14.70 |
| 0.4 | 11.55 | 21.14 | 18.80 |
| 0.6 | 13.30 | 24.38 | 21.79 |
| 0.8 | 14.82 | 27.16 | 24.16 |
| 1.0 | 15.94 | 29.48 | 26.46 |
| 1.2 | 16.96 | 31.56 | 28.14 |
| 1.4 | 17.80 | 33.41 | 29.58 |
| 1.6 | 18.59 | 35.26 | 31.32 |
| 1.8 | 19.32 | 36.81 | 32.44 |
| 2.0 | 20.11 | 38.35 | 33.94 |

A consideration of the above-described embodiments will indicate that the present invention is very simple but nevertheless results in significant improvement to a linear array electrode for use in a flowcell detector in liquid chromatography. It will be understood that the foregoing embodiments are illustrative of the invention and should not be considered as limiting and that other embodiments of the invention are possible without departing from the invention's spirit, or from the scope of the appended claims.

What is claimed is:

1. A linear array electrode comprising:
    an electrically conductive member having a plurality of parallel, longitudinally-extending array elements with each element being spaced from an adjacent array element by a groove and having a substantially flat longitudinally-extending conduction surface with a width between grooves of 10–100 micrometers, wherein each groove extends longitudinally in a direction substantially parallel to the array elements and the conduction surfaces are substantially parallel and coplanar with respect to each other, said electrically conductive member being formed from glassy carbon;
    an insulating member in which said conductive member is partially embedded;
    an insulating embedment filling each of the grooves to a level flush with the conduction surface of each array element, whereby said electrically conductive member is exposed substantially only at the conduction surfaces; and
    means for connecting said electrically conductive member to a source of electric potential.

2. The linear array electrode of claim 1, wherein said electrically conductive member has a rectangular base portion with the array elements being located on one surface of the base portion.

3. The linear array electrode of claim 2, wherein said means for connecting further comprises:
    a coupling extending through said insulating element into contact with the rectangular base of said electrically conductive member at a location distal from the conduction surfaces of said array elements.

4. The linear array electrode of claim 1, wherein said means for connecting comprises:
    a coupling extending through said insulating element into contact with said electrically conductive member.

5. The linear array electrode of claim 4, wherein the coupling is a metallic screw with its head exposed and its tip in contact with said electrically conductive member.

6. The linear array electrode of claim 4, wherein said means for connecting further comprises:
    a wire electrically connecting the coupling with the source of electrical potential.

7. The linear array electrode of claim 1, wherein said insulating embedment is an epoxy resin.

8. In an electrochemical flow cell for use in liquid chromatography, the improvement comprising a linear array electrode comprising:
    an electrically conductive member having a plurality of parallel, longitudinally-extending array elements with each element being spaced from an adjacent array element by a groove and having a substantially flat, longitudinally-extending conduction surface with a width between grooves of 10–100 micrometers, wherein each groove extends longitudinally in a direction substantially parallel to the array elements and the conduction surfaces are substantially parallel and coplanar with respect to each other, said electrically conductive member being formed from glassy carbon;
    an insulating member in which said conductive member is partially embedded;
    an insulating embedment filling each of the grooves to a level flush with the conduction surface of each array element, whereby said electrically conductive member is exposed substantially only at the conduction surfaces; and
    means for connecting said electrically conductive member to a source of electric potential.

9. The electrochemical flow cell of claim 8, wherein said flow cell further comprises:

a wall spaced from and having a surface substantially parallel to the conduction surfaces of said linear array electrode, whereby a narrow, liquid sample flow passage is formed between the wall and the conduction surfaces.

10. The electrochemical flow cell of claim 8, wherein said electrically conductive member has a rectangular base portion with the array elements located on one surface of the base portion.

11. The electrochemical flow cell of claim 10, wherein said means for connecting comprises:

a coupling in contact with the rectangular base portion at a location distal from the conduction surfaces and extending through said insulating element.

12. The electrochemical flow cell of claim 11, wherein said means for connecting further comprises:

a wire electrically connecting the coupling with the source of electrical potential.

13. The electrical flow cell of claim 8, wherein said insulating embedment is an epoxy resin.

* * * * *